US010576081B2

(12) United States Patent
Chang et al.

(10) Patent No.: US 10,576,081 B2
(45) Date of Patent: Mar. 3, 2020

(54) SELF-EMISSIVE DISPLAY WITH SWITCHABLE RETARDER FOR HIGH CONTRAST

(71) Applicant: Apple Inc., Cupertino, CA (US)

(72) Inventors: Shih Chang Chang, Cupertino, CA (US); Cheng Chen, San Jose, CA (US); Chin-Wei Lin, Cupertino, CA (US); Donghee Nam, Cupertino, CA (US); Meng-Huan Ho, Cupertino, CA (US); Minhyuk Choi, Cupertino, CA (US); Rui Liu, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 520 days.

(21) Appl. No.: 14/986,148

(22) Filed: Dec. 31, 2015

(65) Prior Publication Data

US 2017/0053602 A1 Feb. 23, 2017

Related U.S. Application Data

(60) Provisional application No. 62/207,823, filed on Aug. 20, 2015.

(51) Int. Cl.

| | |
|---|---|
| ***G09G 3/3208*** | (2016.01) |
| ***A61K 31/513*** | (2006.01) |
| ***G09G 3/36*** | (2006.01) |

(52) U.S. Cl.

CPC ......... *A61K 31/513* (2013.01); *G09G 3/3208* (2013.01); *G09G 3/3648* (2013.01); *G09G 2300/023* (2013.01); *G09G 2300/0426* (2013.01); *G09G 2320/066* (2013.01)

(58) Field of Classification Search

CPC combination set(s) only.
See application file for complete search history.

(56) References Cited

U.S. PATENT DOCUMENTS

| | | | | |
|---|---|---|---|---|
| 6,008,871 A * | 12/1999 | Okumura | G02F 1/13362 | 349/61 |
| 2003/0156087 A1* | 8/2003 | Boer | G02F 1/13338 | 345/92 |
| 2004/0051827 A1* | 3/2004 | Hinata | G02F 1/133528 | 349/113 |
| 2006/0012737 A1* | 1/2006 | Hirai | G02F 1/13363 | 349/114 |

(Continued)

*Primary Examiner* — Temesghen Ghebretinsae
*Assistant Examiner* — Sosina Abebe
(74) *Attorney, Agent, or Firm* — Fletcher Yoder, P.C.

(57) ABSTRACT

Systems and electronic displays with improved contrast even under bright-light conditions are provided. Such an electronic display may include a self-emissive pixel (e.g., OLED or μ-LED) with a corresponding liquid crystal switchable retarder pixel. A liquid crystal layer of the switchable retarder pixel may be tuned to an “on” state or an “off” state. In the “on” state, the switchable retarder pixel may allow outside light that enters the pixel to reflect back out of the pixel. This may add to the amount of light that appears to be emitted from that pixel. In the “off” state, the switchable retarder pixel may block the outside light that enters the pixel from reflecting back out of the pixel. This may reduce the amount of light that appears to be emitted from that pixel. Selectively controlling the switchable retarder pixels may allow for increased contrast even under bright-light conditions.

30 Claims, 14 Drawing Sheets

(56) References Cited

U.S. PATENT DOCUMENTS

2008/0030656 A1* 2/2008 Watson ............. G02F 1/133536 349/96
2008/0055519 A1* 3/2008 Battersby ............. G09G 3/3648 349/68
2008/0055535 A1* 3/2008 Chiba .................... C09K 19/60 349/165
2012/0306771 A1* 12/2012 Chen ..................... G06F 3/0418 345/173
2013/0215093 A1* 8/2013 Bergquist ............. G09G 3/3208 345/207
2013/0329288 A1* 12/2013 Yim .................... H01L 51/5281 359/483.01
2014/0071539 A1* 3/2014 Gao ................... G02B 27/0172 359/630
2014/0160177 A1* 6/2014 Smith .................. G09G 3/3659 345/690
2015/0138457 A1* 5/2015 Kroon ................ G02B 27/2214 349/15
2015/0228089 A1* 8/2015 Perdices-Gonzalez ...................... G09G 3/348 345/592

* cited by examiner

| | | | | | |
|---|---|---|---|---|---|
| SE: 255<br>LC: ON | SE: 255<br>LC: ON | SE: 255<br>LC: ON | SE: 255<br>LC: ON | SE: 200<br>LC: ON | SE: 160<br>LC: ON |
| SE: 255<br>LC: ON | SE: 255<br>LC: ON | SE: 255<br>LC: ON | SE: 255<br>LC: ON | SE: 180<br>LC: ON | SE: 129<br>LC: ON |
| SE: 255<br>LC: ON | SE: 255<br>LC: ON | SE: 255<br>LC: ON | SE: 170<br>LC: ON | SE: 120<br>LC: ON | SE: 100<br>LC: ON |
| SE: 255<br>LC: ON | SE: 255<br>LC: ON | SE: 160<br>LC: ON | SE: 100<br>LC: ON | SE: 80<br>LC: ON | SE: 30<br>LC: ON |
| SE: 255<br>LC: ON | SE: 255<br>LC: ON | SE: 92<br>LC: ON | SE: 40<br>LC: ON | SE: 0<br>LC: OFF | SE: 0<br>LC: OFF |

...

| | | | | | | |
|---|---|---|---|---|---|---|
| SE: 255<br>LC: ON | SE: 255<br>LC: ON | SE: 255<br>LC: ON | SE: 255<br>LC: ON | SE: 200 | SE: 160 | |
| SE: 255<br>LC: ON | SE: 255<br>LC: ON | SE: 255<br>LC: ON | SE: 255<br>LC: ON | SE: 180<br>LC: ON | SE: 129<br>LC: ON | |
| SE: 255<br>LC: ON | SE: 255<br>LC: ON | SE: 255<br>LC: ON | SE: 170<br>LC: ON | SE: 120<br>LC: OFF | SE: 100<br>LC: OFF | • • • |
| SE: 255<br>LC: ON | SE: 255<br>LC: ON | SE: 160<br>LC: ON | SE: 100<br>LC: OFF | SE: 80<br>LC: OFF | SE: 30<br>LC: OFF | |
| SE: 255<br>LC: ON | SE: 255<br>LC: ON | SE: 92<br>LC: OFF | SE: 40<br>LC: OFF | SE: 0<br>LC: OFF | SE: 0<br>LC: OFF | |

SELF-EMISSIVE DISPLAY WITH SWITCHABLE RETARDER FOR HIGH CONTRAST

CROSS REFERENCE TO RELATED APPLICATIONS

This application is a Non-Provisional patent application of U.S. Provisional Patent Application No. 62/207,823, entitled "Self-Emissive Display with Switchable Retarder for High Contrast", filed Aug. 20, 2015, which are herein incorporated by reference.

BACKGROUND

This disclosure relates to a high-contrast self-emissive electronic display and, more particularly, to a self-emissive electronic display that includes a switchable retarder to selectively block or permit outside light to reflect into and out of pixels of the display to improve contrast.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Many electronic devices include electronic displays. One form of electronic display with particularly high contrast under many conditions is a self-emissive display. Organic light emitting diode (OLED) displays and micro-light-emitting-diode (μ-LED) displays are examples of self-emissive displays that use LEDs as pixels. A self-emissive display has pixels that individually generate their own light, rather than modulating light deriving from a backlight. As such, displaying dark gray levels or the color black involve emitting very little to no light at all. Since the maximum image contrast ratio is based on the maximum amount of light that is emitted by a pixel as compared to a minimum amount of light that is emitted by the pixel, self-emissive displays generally produce images with excellent contrast ratios.

There are certain situations, however, where the contrast ratio of a self-emissive display may be less impressive. Under conditions with large quantities of outside light—such as outdoors on a bright day—the contrast ratio may be substantially lower. Under conditions like these, large quantities of outside light enter the pixels of the display and/or are reflected off of the electronic display. This adds light to both the brightest pixels of the image and the darkest pixels of the image, lowering the contrast ratio. That is, the difference between the brightest pixels and the darkest pixels may be significantly less than under conditions with less outside light. Although it may be possible to increase the amount of light emitted by the brightest pixels by increasing the drive strength of the self-emissive pixels, doing so may reduce the life of the pixels and draw substantially more energy.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

To improve the contrast of a self-emissive electronic display in bright-light conditions, switchable retarder pixels may selectively block or permit outside light to reflect out of pixels of the display. For example, each self-emissive pixel (e.g., OLED or μ-LED) may have a corresponding liquid crystal switchable retarder pixel. A liquid crystal layer of the switchable retarder pixel may be tuned to an "on" state or an "off" state. In the "on" state, the switchable retarder pixel may allow outside light that enters the pixel to reflect back out of the pixel. This may add to the amount of light that appears to be emitted from that pixel. In the "off" state, the switchable retarder pixel may block the outside light that enters the pixel from reflecting back out of the pixel. This may reduce the amount of light that appears to be emitted from that pixel. By selectively allowing outside light to contribute to brighter pixels of the display (e.g., pixels that are on) while blocking the outside light from contributing to darker pixels of the display (e.g., pixels that are off), the contrast of the electronic display may be enhanced. This effect may be particularly noticeable under bright-light conditions.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which:

FIG. 16 is a pixel map illustrating setting switchable retarder pixels to an "off" state when the self-emissive pixels are less than a threshold gray level, in accordance with an embodiment;

DETAILED DESCRIPTION

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but may nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

This disclosure relates to using switchable retarder pixels to increase the contrast of a self-emissive display. Each switchable retarder pixel may selectively allow or block outside light from adding to the light emitted by one or more self-emissive pixels. In bright light, such as an ambient amount of light outdoors on a sunny day, the ambient outside light may be selectively blocked by the switchable retarder pixels from contributing to dark self-emissive pixels. The outside light may be permitted, however, to contribute to brighter self-emissive pixels.

Figure 1:
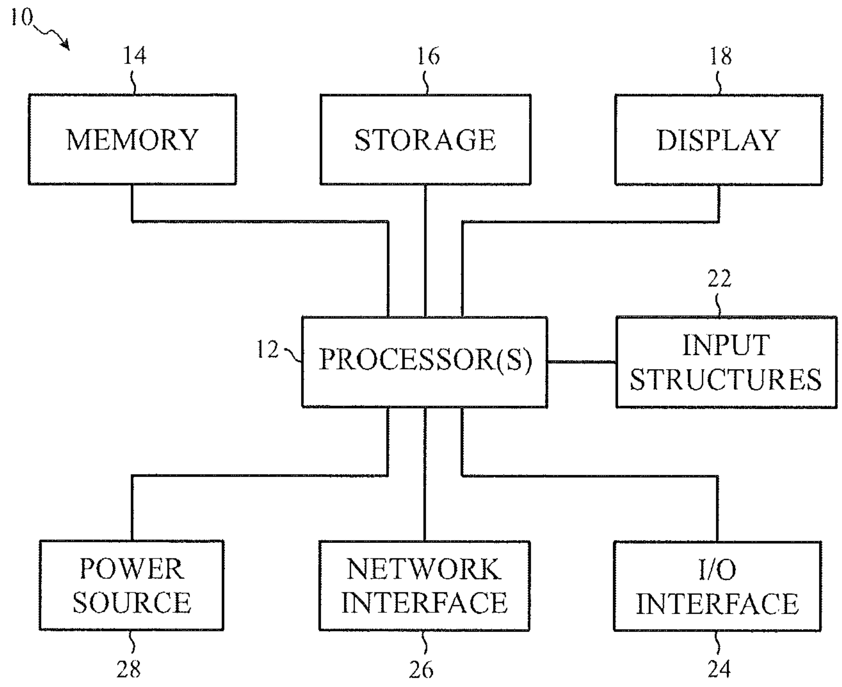
FIG. 1 is a schematic block diagram of an electronic device including a high-contrast self-emissive display, in accordance with an embodiment.

Turning first to FIG. 1, an electronic device 10 according to an embodiment of the present disclosure may include, among other things, one or more processor(s) 12, memory 14, nonvolatile memory 16, a display 18 input structures 22, an input/output (I/O) interface 24, network interfaces 26, and a power source 28. The various functional blocks shown in FIG. 1 may include hardware elements (including circuitry), software elements (including computer code stored on a computer-readable medium) or a combination of both hardware and software elements. It should be noted that FIG. 1 is merely one example of a particular implementation and is intended to illustrate the types of components that may be present in electronic device 10.

Figure 2:
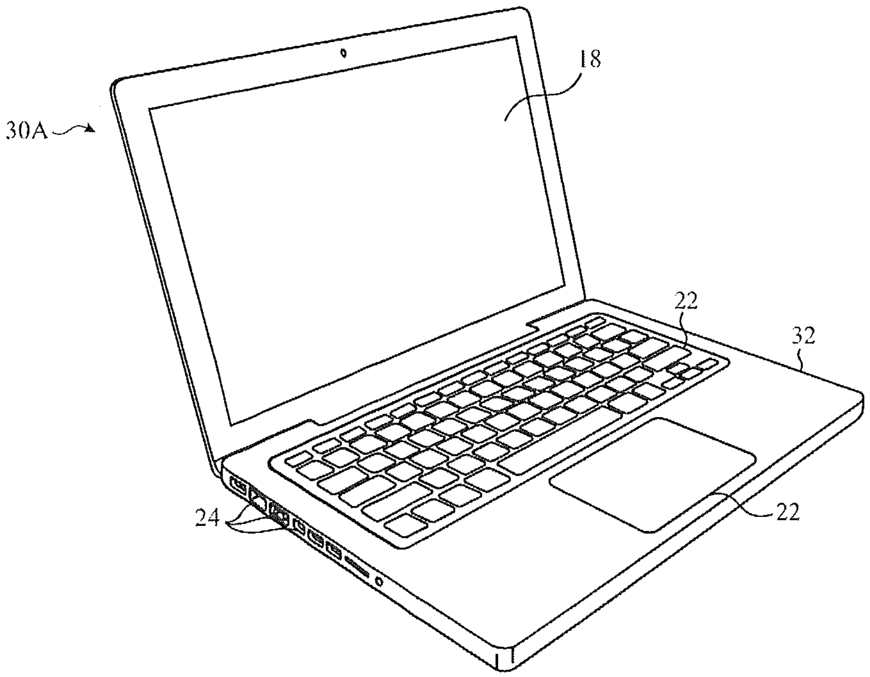
FIG. 2 is a perspective view of a notebook computer representing an embodiment of the electronic device of FIG. 1.
Figure 3:
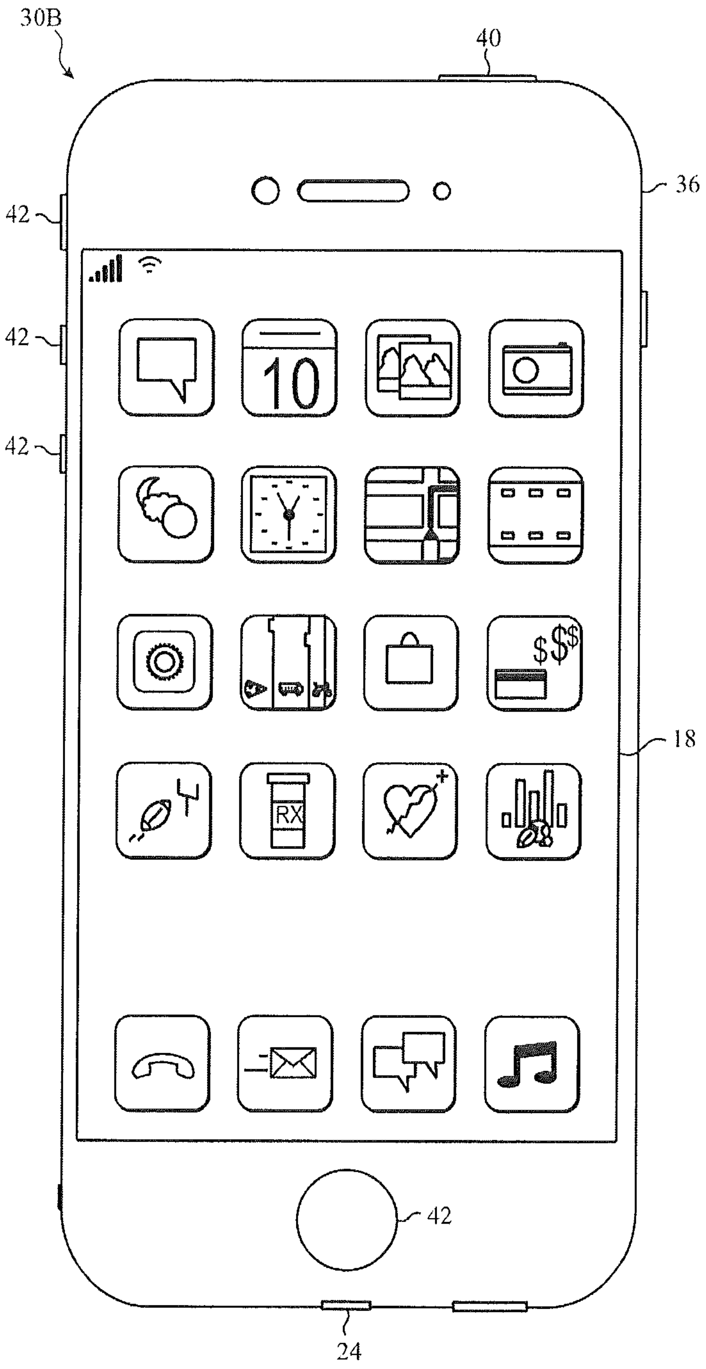
FIG. 3 is a front view of a hand-held device representing another embodiment of the electronic device of FIG. 1.
Figure 4:
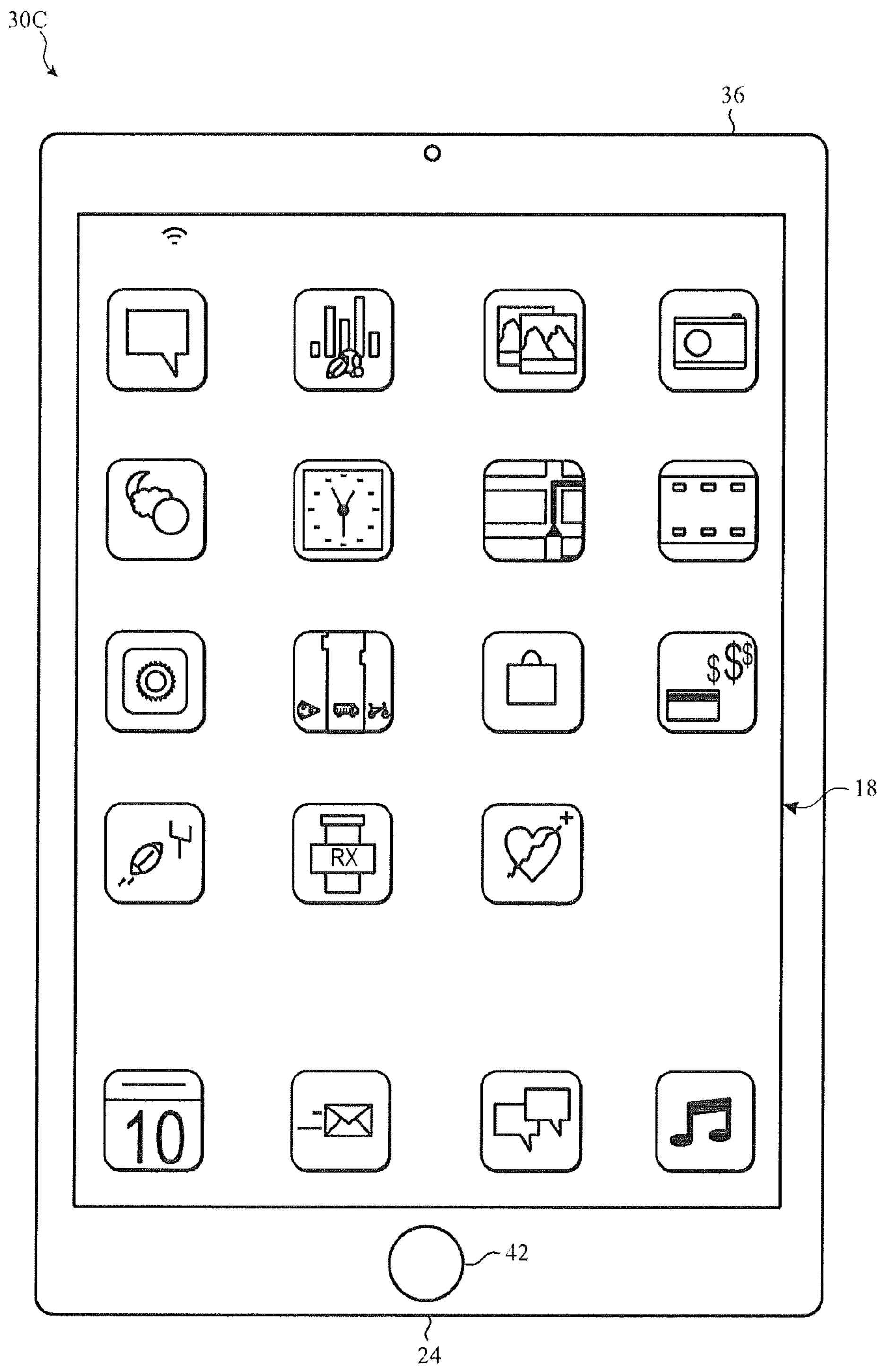
FIG. 4 is a front view of another hand-held device representing another embodiment of the electronic device of FIG. 1.
Figure 5:
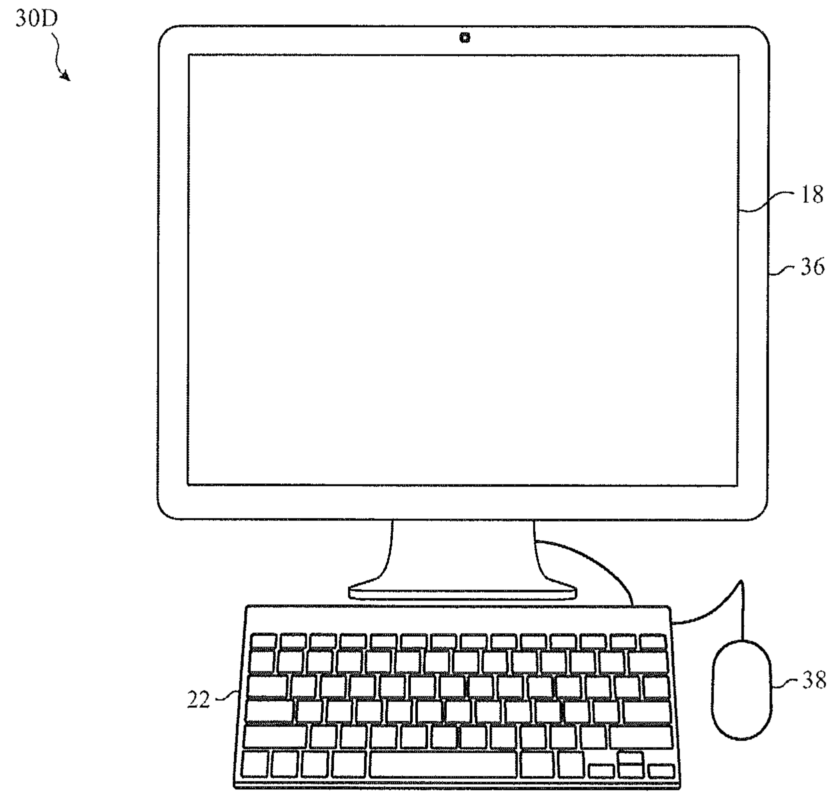
FIG. 5 is a front view of a desktop computer representing another embodiment of the electronic device of FIG. 1.

By way of example, the electronic device 10 may represent a block diagram of the notebook computer depicted in FIG. 2, the handheld device depicted in FIG. 3, the desktop computer depicted in FIG. 4, the wearable electronic device depicted in FIG. 5, or similar devices. It should be noted that the processor(s) 12 and/or other data processing circuitry may be generally referred to herein as "data processing circuitry." Such data processing circuitry may be embodied wholly or in part as software, firmware, hardware, or any combination thereof. Furthermore, the data processing circuitry may be a single contained processing module or may be incorporated wholly or partially within any of the other elements within the electronic device 10.

In the electronic device 10 of FIG. 1, the processor(s) 12 and/or other data processing circuitry may be operably coupled with the memory 14 and the nonvolatile memory 16 to perform various algorithms. Such programs or instructions executed by the processor(s) 12 may be stored in any suitable article of manufacture that may include one or more tangible, computer-readable media at least collectively storing the instructions or routines, such as the memory 14 and the nonvolatile memory 16. The memory 14 and the nonvolatile memory 16 may include any suitable articles of manufacture for storing data and executable instructions, such as random-access memory, read-only memory, rewritable flash memory, hard drives, and optical discs. Also, programs (e.g., an operating system) encoded on such a computer program product may also include instructions that may be executed by the processor(s) 12 to enable the electronic device 10 to provide various functionalities.

As will be discussed further below, the display 18 may include self-emissive pixels such as organic light emitting diodes (OLEDs) or micro-light-emitting-diodes (μ-LEDs). In addition, the display 18 may include switchable retarder pixels, each of which corresponds to one or more of the self-emissive pixels. The switchable retarder pixels may use liquid crystal materials to selectively retard or permit outside light. Using the switchable retarder pixels may thus allow for a high-contrast mode of operation of the display 18.

The input structures 22 of the electronic device 10 may enable a user to interact with the electronic device 10 (e.g., pressing a button to increase or decrease a volume level). The I/O interface 24 may enable electronic device 10 to interface with various other electronic devices, as may the network interfaces 26. The network interfaces 26 may include, for example, interfaces for a personal area network (PAN), such as a Bluetooth network, for a local area network (LAN) or wireless local area network (WLAN), such as an 802.11x Wi-Fi network, and/or for a wide area network (WAN), such as a $3^{rd}$ generation (3G) cellular network, $4^{th}$ generation (4G) cellular network, or long term evolution (LTE) cellular network. The network interface 26 may also include interfaces for, for example, broadband fixed wireless access networks (WiMAX), mobile broadband Wireless networks (mobile WiMAX), asynchronous digital subscriber lines (e.g., ADSL, VDSL), digital video broadcasting-terrestrial (DVB-T) and its extension DVB Handheld (DVB-H), ultra Wideband (UWB), alternating current (AC) power lines, and so forth.

In certain embodiments, the electronic device 10 may take the form of a computer, a portable electronic device, a wearable electronic device, or other type of electronic device. Such computers may include computers that are generally portable (such as laptop, notebook, and tablet computers) as well as computers that are generally used in one place (such as conventional desktop computers, workstations and/or servers). In certain embodiments, the electronic device 10 in the form of a computer may be a model of a MacBook®, MacBook® Pro, MacBook Air®, iMac®, Mac® mini, or Mac Pro® available from Apple Inc. By way of example, the electronic device 10, taking the form of a notebook computer 30A, is illustrated in FIG. 2 in accordance with one embodiment of the present disclosure. The depicted computer 30A may include a housing or enclosure 32, a display 18, input structures 22, and ports of an I/O interface 24. In one embodiment, the input structures 22 (such as a keyboard and/or touchpad) may be used to interact with the computer 30A, such as to start, control, or operate a GUI or applications running on computer 30A. For example, a keyboard and/or touchpad may allow a user to navigate a user interface or application interface displayed on display 18.

FIG. 3 depicts a front view of a handheld device 30B, which represents one embodiment of the electronic device 10. The handheld device 34 may represent, for example, a portable phone, a media player, a personal data organizer, a handheld game platform, or any combination of such devices. By way of example, the handheld device 34 may be a model of an iPod® or iPhone® available from Apple Inc. of Cupertino, Calif.

The handheld device 30B may include an enclosure 36 to protect interior components from physical damage and to shield them from electromagnetic interference. The enclosure 36 may surround the display 18, which may display indicator icons 39. The indicator icons 39 may indicate, among other things, a cellular signal strength, Bluetooth connection, and/or battery life. The I/O interfaces 24 may open through the enclosure 36 and may include, for example, an I/O port for a hard wired connection for charging and/or content manipulation using a standard connector and protocol, such as the Lightning connector provided by Apple Inc., a universal service bus (USB), or other similar connector and protocol.

User input structures 42, in combination with the display 18, may allow a user to control the handheld device 30B. For example, the input structure 40 may activate or deactivate the handheld device 30B, the input structure 42 may navigate user interface to a home screen, a user-configurable application screen, and/or activate a voice-recognition feature of the handheld device 30B, the input structures 42 may provide volume control, or may toggle between vibrate and ring modes. The input structures 42 may also include a microphone may obtain a user's voice for various voice-related features, and a speaker may enable audio playback and/or certain phone capabilities. The input structures 42 may also include a headphone input may provide a connection to external speakers and/or headphones.

FIG. 4 depicts a front view of another handheld device 30C, which represents another embodiment of the electronic device 10. The handheld device 30C may represent, for example, a tablet computer, or one of various portable computing devices. By way of example, the handheld device 30C may be a tablet-sized embodiment of the electronic device 10, which may be, for example, a model of an iPad® available from Apple Inc. of Cupertino, Calif.

Turning to FIG. 5, a computer 30D may represent another embodiment of the electronic device 10 of FIG. 1. The computer 30D may be any computer, such as a desktop computer, a server, or a notebook computer, but may also be a standalone media player or video gaming machine. By way of example, the computer 30D may be an iMac®, a MacBook®, or other similar device by Apple Inc. It should be noted that the computer 30D may also represent a personal computer (PC) by another manufacturer. A similar enclosure 36 may be provided to protect and enclose internal components of the computer 30D such as the display 18. In certain embodiments, a user of the computer 30D may interact with the computer 30D using various peripheral input devices, such as the input structures 22 or mouse 38, which may connect to the computer 30D via a wired and/or wireless I/O interface 24.

Figure 6:
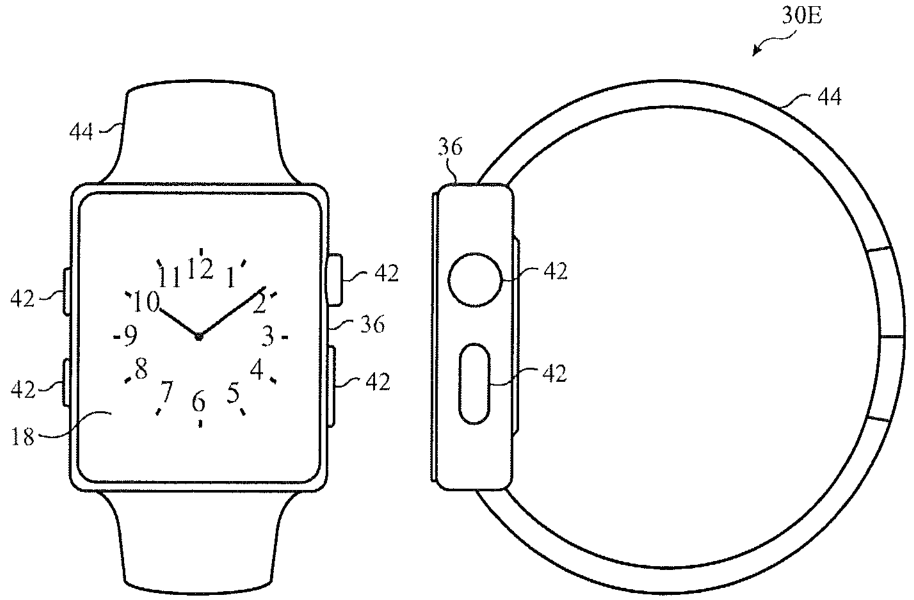
FIG. 6 is a front view of a wearable electronic device representing another embodiment of the electronic device of FIG. 1.

Similarly, FIG. 6 depicts a wearable electronic device 30E representing another embodiment of the electronic device 10 of FIG. 1 that may be configured to operate using the techniques described herein. By way of example, the wearable electronic device 30E, which may include a wristband 43, may be an Apple Watch® by Apple, Inc. However, in other embodiments, the wearable electronic device 30E may include any wearable electronic device such as, for example, a wearable exercise monitoring device (e.g., pedometer, accelerometer, heart rate monitor), or other device by another manufacturer. The display 18 of the wearable electronic device 30E may include a touch screen, which may allow users to interact with a user interface of the wearable electronic device 30E.

The self-emissive electronic display 18 of this disclosure may operate in a high-contrast mode to account for bright ambient light. First, the contrast of the electronic display 18 may be generally understood to represent the ratio of the amount of light from the brightest pixel of an image on the display 18 (e.g., gray level 255 of an 8-bit image) to the amount of light from the darkest pixel of the image on the display (e.g., gray level 0 of an 8-bit image). When outside light is considered (and when the electronic display 18 is not operating in the high-contrast mode), the contrast ratio may be generally described according to the following equation:

$$\text{Contrast} = \frac{I_{max}}{I_{min}} = \frac{I_{emitted} + I_{reflected}}{I_{reflected}}, \quad \text{(Eq. 1)}$$

where $I_{max}$ is the maximum amount of light emitted by the brightest pixel (e.g., a gray level 255 for an 8-bit image data) and $I_{min}$ represents the least amount of light of any pixel (e.g., gray level 0). In practice, the reflected light $I_{reflected}$ may add to both light and dark pixels when the electronic display 18 is not operating in a high-contrast mode.

Figure 7:
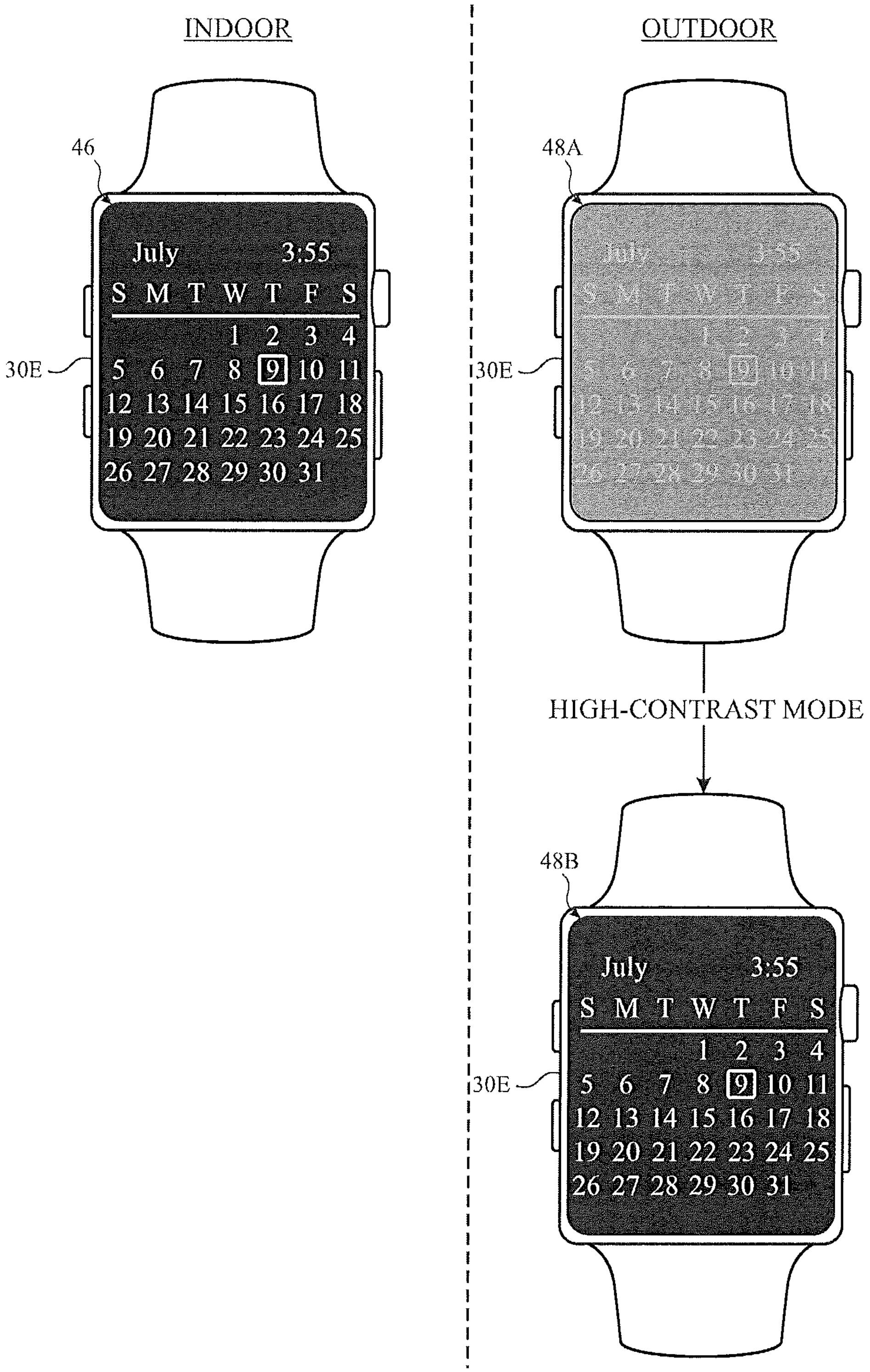
FIG. 7 is an example of operating a self-emissive display in a high-contrast mode, in accordance with an embodiment.

Thus, as shown in FIG. 7, when the electronic display 18 is used in relatively low-ambient-light conditions—such as when the wearable device 30E is worn indoors (numeral 46)—the electronic display 18 may have good contrast. This may be the case even when not operating in the high-contrast mode. In an outdoor use case, however, there may be a significant amount of outside light (numeral 48A). Considering Equation 1 above, it may be understood that the contrast ratio of the electronic display 18 may be greatly diminished under these conditions. In effect, an equal amount of outdoor (reflected) light $I_{reflected}$ may be present in both bright and dark pixels. Under bright ambient-light conditions, the outdoor (reflected) light $I_{reflected}$ may come to dominate the total amount of light on both the numerator and the denominator, reducing the contrast.

To increase contrast, even under high-ambient-light conditions (numeral 48B), the electronic display 18 may operate in a high-contrast mode. In the high-contrast mode, switchable retarder pixels may block (e.g., absorb) at least some of the light on darker pixels of the image displayed on the display 18. The switchable retarder pixels may permit at least some of the light that reflects off the brighter pixels of the image displayed on the display 18. In effect, this increases the amount of the reflected light $I_{reflected}$ in the numerator of Equation 1 in relation to the amount of the reflected light $I_{reflected}$ in the denominator of Equation 1. This has the effect of increasing the apparent contrast.

Figure 8:
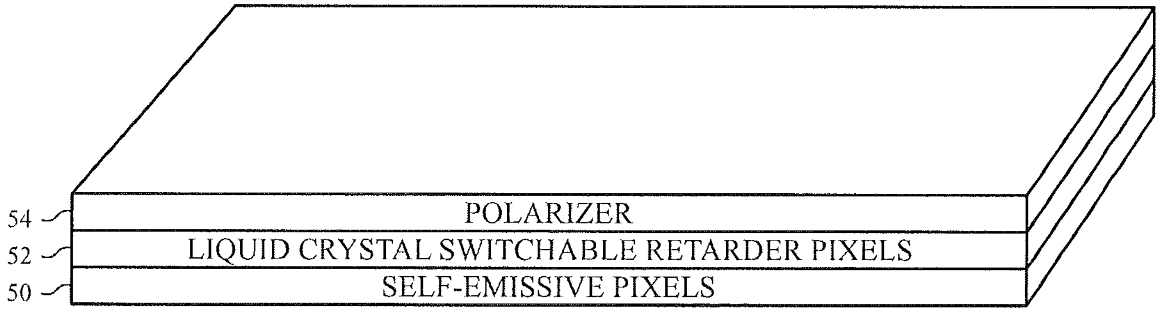
FIG. 8 is a schematic view of layers of the electronic display of this disclosure, in accordance with an embodiment.

The electronic display 18 may operate in the high-contrast mode using a self-emissive pixel array 50 with corresponding liquid crystal switchable retarder pixel array 52 under a polarizer 54, as shown in FIG. 8. The liquid crystal switchable retarder pixel array 52 may selectively cause reflected light from outside the electronic display 18 to be emitted or blocked depending on the amount of light being emitted by the self-emissive pixel 50 array. In one example, pixels of the liquid crystal switchable retarder pixel array 52 may share 1:1 relationship with the pixels of the self-emissive pixel array 50. In such an example, one pixel of the self-emissive pixel array 50 may correspond directly with one pixel of the liquid crystal switchable retarder pixel array 52. Alternatively, one pixel of the liquid crystal switchable retarder pixel array 52 may correspond to multiple pixels of the self-emissive pixel array 50. Each pixel of the liquid crystal switchable retarder pixels 52 may correspond, for example, to three pixels of the self-emissive pixel array 50 (e.g., one switchable retarder pixel to red, green, and blue self-emissive pixels). Note that individual pixels of specific colors may be sometimes referred to as subpixels, and collections of one of each of these subpixels may be sometimes collectively referred to as a superpixel, but subpixels and superpixels may also be referred to as "pixels."

Figure 9:
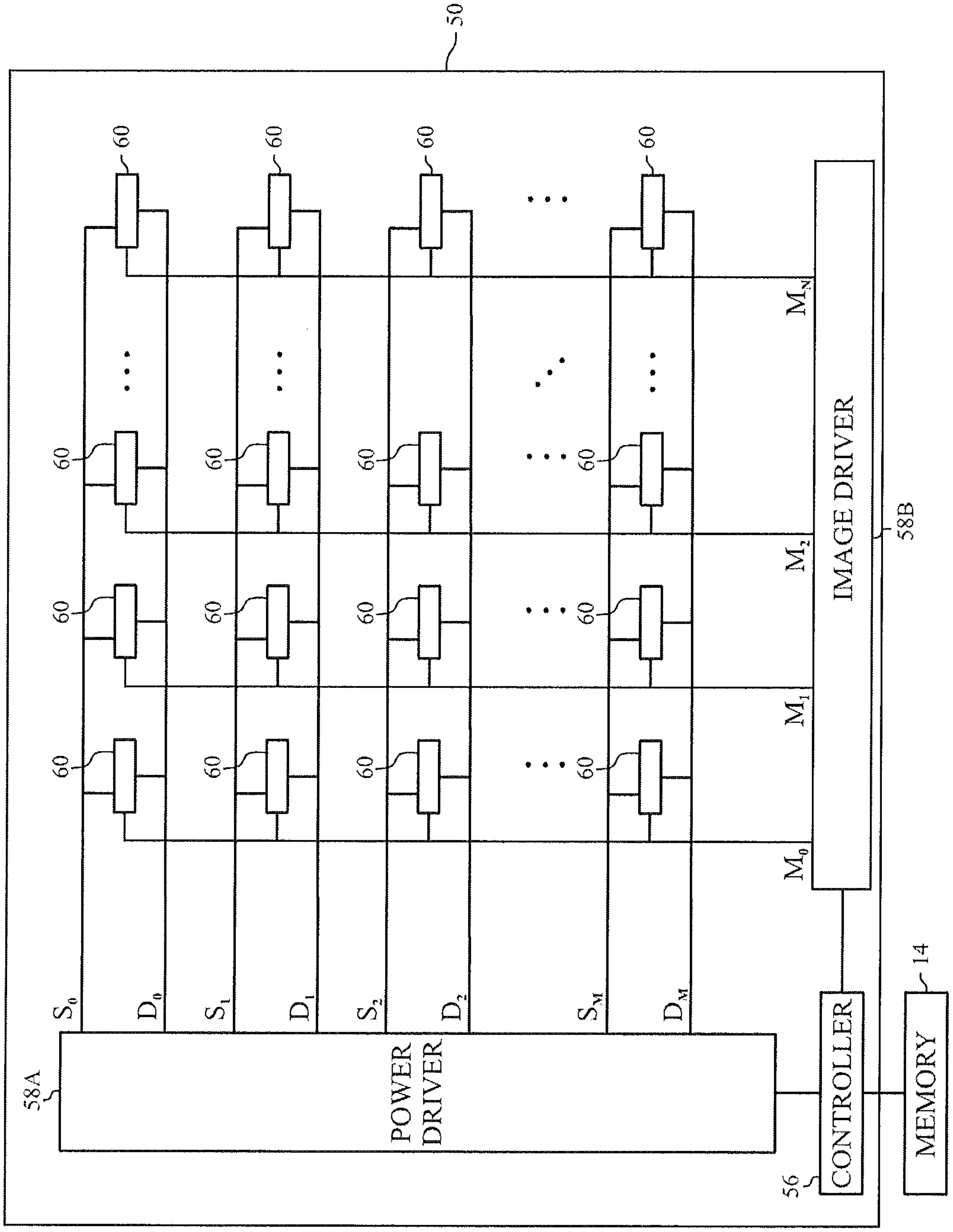
FIG. 9 is a circuit diagram of an array of self-emissive pixels of the electronic display, in accordance with an embodiment.

An example of the self-emissive pixel array 50 appears in FIG. 9. The self-emissive pixel array 50 is shown having a controller 56, a power driver 58A, an image driver 58B, and an array of self-emissive pixels 60. The self-emissive pixels 60 are driven by the power driver 58A and image driver 58B. Each power driver 58A and image driver 58B may drive one or more self-emissive pixels 60. In some embodiments, the power driver 58A and the image driver 58B may include multiple channels for independently driving multiple self-emissive pixels 60. The self-emissive pixels may include any suitable light-emitting elements, such as organic light emitting diodes (OLEDs), micro-light-emitting-diodes (μ-LEDs), and so forth.

The power driver 58A may be connected to the self-emissive pixels 60 by way of scan lines $S_0$, $S_1$, . . . $S_{m-1}$, and $S_m$ and driving lines $D_0$, $D_1$, . . . $D_{m-1}$, and $D_m$. The self-emissive pixels 60 receive on/off instructions through the scan lines $S_0$, $S_1$, . . . $S_{m-1}$, and $S_m$ and generate driving currents corresponding to data voltages transmitted from the driving lines $D_0$, $D_1$, . . . $D_{m-1}$, and $D_m$. The driving currents are applied to each self-emissive pixel 60 to emit light according to instructions from the image driver 58B through driving lines $M_0$, $M_1$, . . . $M_{n-1}$, and $M_m$ Both the power driver 58A and the image driver 58B transmit voltage signals through respective driving lines to operate each self-emissive pixel 60 at a state determined by the controller 56 to emit light. Each driver may supply voltage signals at a duty cycle and/or amplitude sufficient to operate each self-emissive pixel 60.

The individual self-emissive pixels 60 may be arranged in groups within the display 18 to form superpixels. Superpixels may be understood to include groups of self-emissive pixels 60 (e.g., three or four) emitting different colors, particularly complementary colors such as red, cyan, green, magenta, blue, yellow, white, and combinations thereof. These light colors from each self-emissive pixel 60 may be mixed according to instructions from the controller 56 to create specific colors, including white, for each superpixel. Together, the specific colors for each pixel of the self-emissive pixel array 50 form an image on the self-emissive pixel array 50.

The controller 56 may control the color of the self-emissive pixels 60 using image data generated by the processor(s) 12 and stored into the memory 14 or provided directly from the processor(s) 12 to the controller 56. The controller 56 may also determine, when the electronic display is operating in a high-contrast mode, when to selectively allow or block outside light from contributing to the light of a self-emissive pixel 60 by controlling the liquid crystal switchable retarder pixel array 52.

Figure 10:
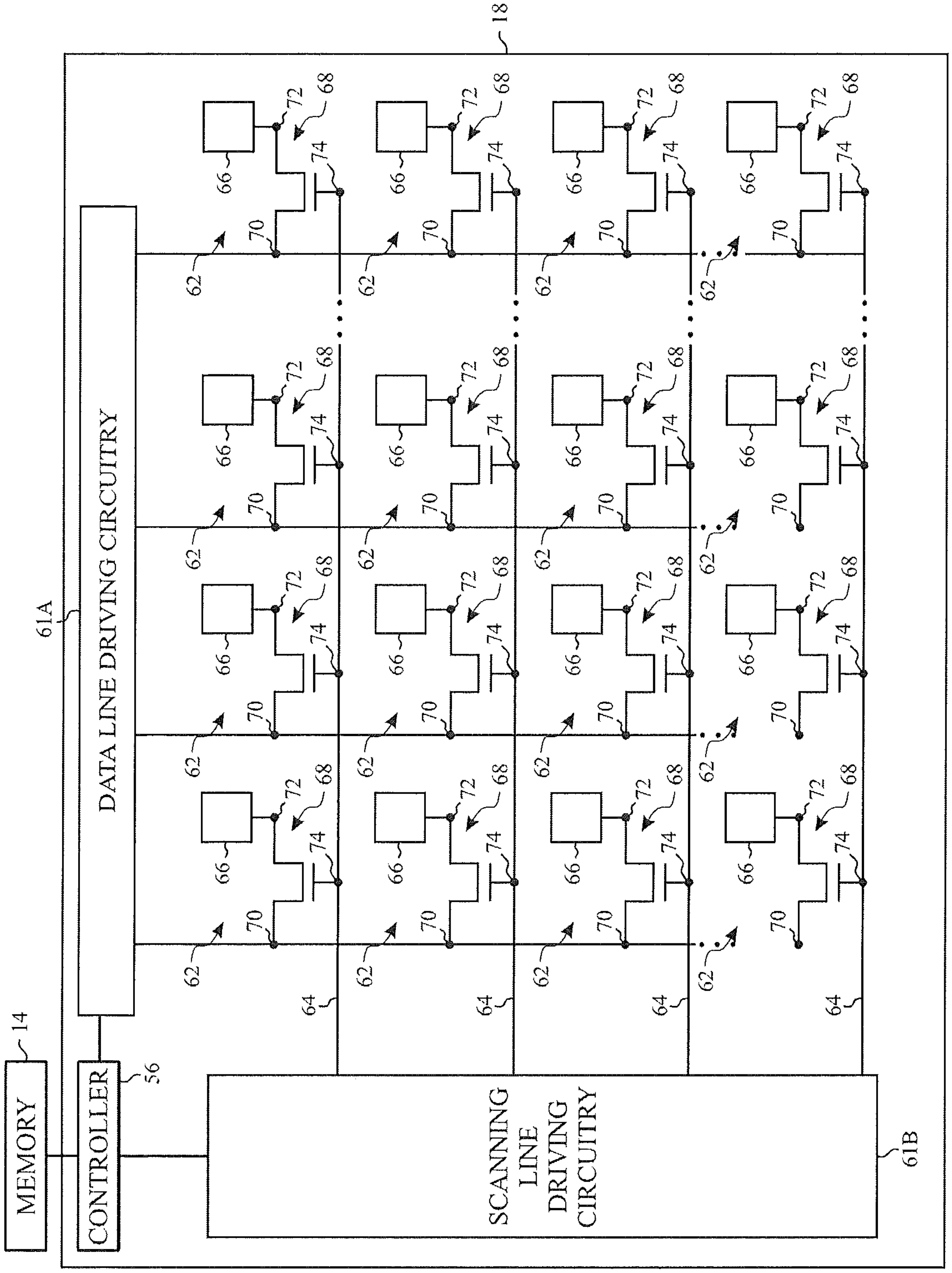
FIG. 10 is a circuit diagram of an array of liquid crystal switchable retarder pixels, in accordance with an embodiment.

FIG. 10 illustrates an example of the liquid crystal switchable retarder pixel array 52. The liquid crystal switchable retarder pixel array 52 includes source line driving circuitry 61A and gate line driving circuitry 61B to selectively control an array of switchable retarder pixels 62. Each switchable retarder pixel 62 includes a pixel electrode 66 and a thin film transistor (TFT) 68 for switching access to the pixel electrode 66. In the depicted embodiment, a source 70 of each TFT 68 is electrically connected to a data line 63 extending from respective source line driving circuitry 61A, and a drain 72 is electrically connected to the pixel electrode 66. Similarly, in the depicted embodiment, a gate 74 of each TFT 68 is electrically connected to a scanning line 64 extending from respective gate line driving circuitry 61B.

Column drivers of the source line driving circuitry 61A send one of two state signals—"on" or "off"—to the switchable retarder pixels 62 via the respective source lines 63. Gate lines 64 may apply gate signals from the gate line driving circuitry 61B to the gate 74 of each TFT 68. Such gate signals may be applied by line-sequence with a predetermined timing or in a pulsed manner. Each TFT 68 serves as a switching element which may be activated and deactivated (i.e., turned on and off) for a predetermined period based on the respective presence or absence of a scanning signal at its gate 74. When activated, a TFT 68 may store the state signal received via a respective data line 63 as a charge in the pixel electrode 66.

The image signals stored at the pixel electrode 66 may be used to generate an electrical field between the respective pixel electrode 66 and a common electrode (VCOM) 76. Such an electrical field may align liquid crystals within a liquid crystal layer to modulate light transmission through the liquid crystal switchable pixel array 52. In conjunction with various color filters, such as red, green, and blue filters, outside light may be permitted to contributed to corresponding red, green, or blue self-emissive pixels 60. A storage capacitor may also be provided in parallel to the liquid crystal capacitor formed between the pixel electrode 66 and the common electrode to prevent leakage of the stored image signal at the pixel electrode 66. For example, such a storage capacitor may be provided between the drain 72 of the respective TFT 68 and a separate capacitor line.

Figure 11:
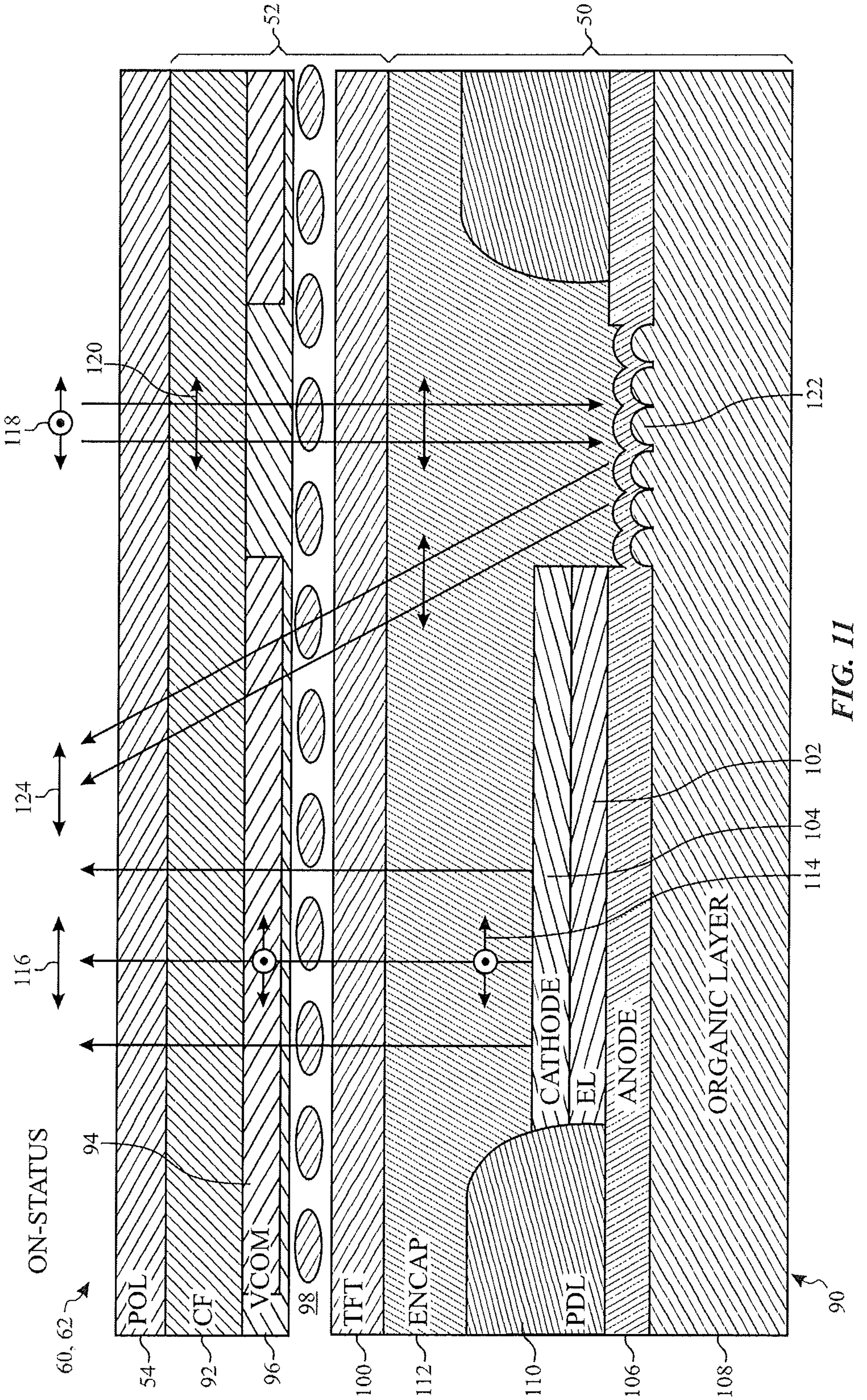
FIG. 11 is a cross-sectional view of a pixel of the electronic display when the pixel is on and the electronic display is in the high-contrast mode, in accordance with an embodiment.
Figure 12:
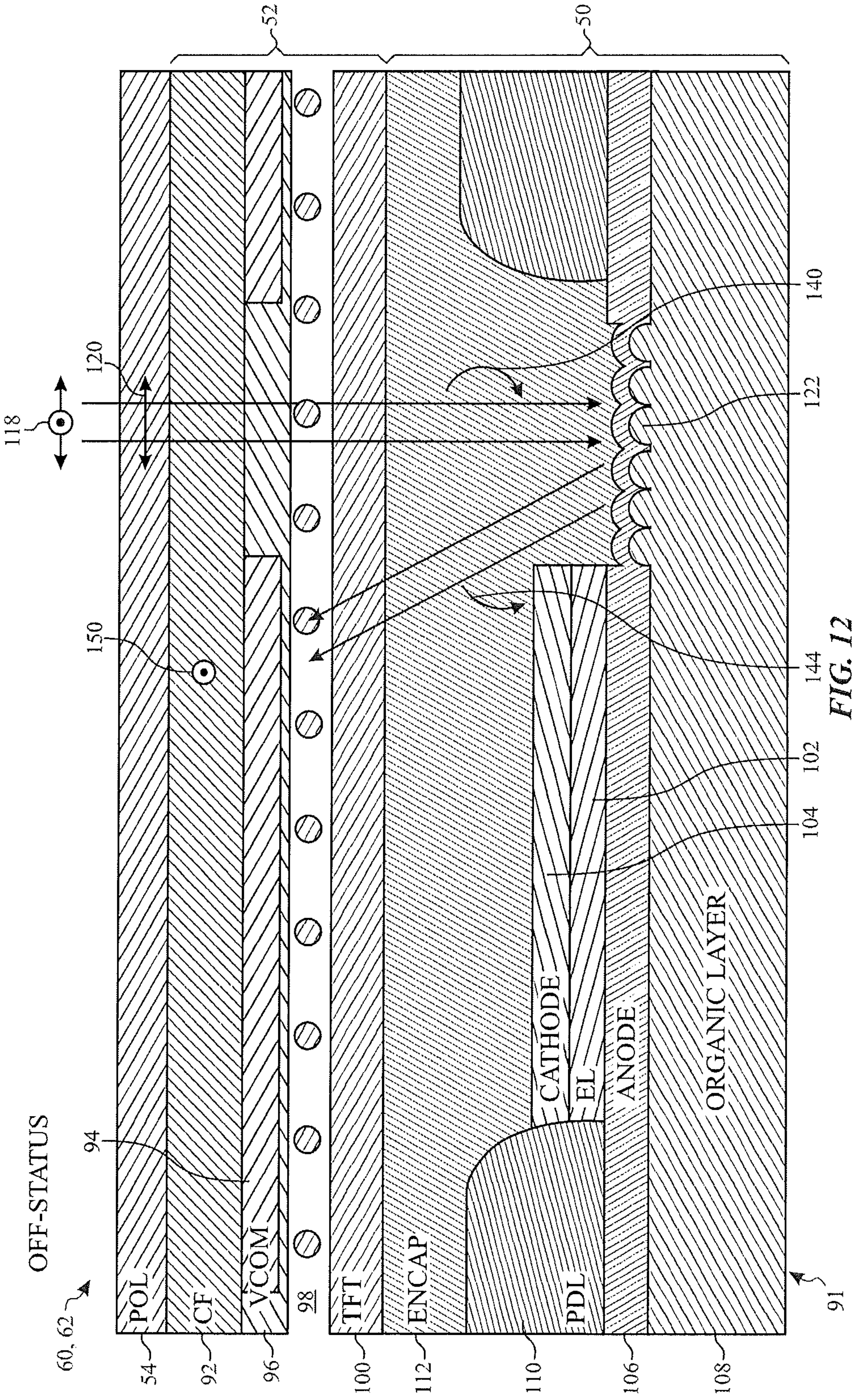
FIG. 12 is a cross-sectional view of a pixel of the electronic display when the pixel is off, in accordance with an embodiment.

A self-emissive pixel 60 may have a corresponding switchable retarder pixel 62, as shown in FIGS. 11 and 12. In FIG. 11, a cross-sectional view of one group of pixels 60, 62 in an "on" state 90 is shown. FIG. 12 shows the operation of the pixels 60, 62 in an "off" state 91. In FIG. 11, the self-emissive pixel array 50 is disposed beneath the liquid crystal switchable retarder pixel array 52. The polarizer layer 54 is disposed above these. The switchable retarder array 52 includes a color filter substrate (CF) 92, a color filter 94 disposed on the CF layer 92, a common voltage (VCOM) layer 96 disposed on the CF layer 92 and the color filter 94, a liquid crystal (LC) layer 98, and a thin film transistor (TFT) layer 100 to control the orientation of the liquid crystal molecules in the LC layer 98.

The self-emissive pixel array 50 includes an electroluminescent (EL) element 102, a cathode 104 disposed above the EL 102, and an anode 106 disposed beneath the EL element 102. These components are disposed over an organic layer 108 and supplied with power by a power distribution line (PDL) 110 covered by an encapsulation layer 112. The self-emissive pixel 60 of the self-emissive pixel array 50 emits substantially non-polarized light 114 that passes out of the self-emissive layer 50 and through the liquid crystal switchable retarder array 52 substantially unchanged, and emitted out of the polarizer layer 54 as polarized light 116.

When the switchable retarder pixel 62 is in the "on" state 90, outside light 118 from outside the display 18 may be permitted to enter and reflect out of the display 18 at the pixel 60, 62. The outside light 118 may pass through the polarizing layer 54 and enter the pixel 60, 62 as polarized outside light 120. The polarized outside light 120 may scatter or reflect off of scattering elements 122, which may operate as a light lens to spread the polarized outside light 120 through the pixel 60, 62. The polarized outside light 120, after reflecting off the scattering elements 122, may pass through the color filter 94, which may filter out wavelengths of the light except for those permitted by that color filter 94. For example, when the pixels 60, 62 form a red pixel, the color filter 94 may be red, and the polarized outside light 120 passing through the color filter 94 that exits the color filter 94 may also be red.

The polarized outside light 120 is allowed to pass through the LC layer 98 because the LC layer 98 is tuned to the "on" state. In the "on" state, the TFT layer 100 causes an electric field to form in the LC layer 98 that is substantially parallel to the transmissive axis of the polarizer 54. Therefore, the polarized outside light 120 may be substantially unaffected by the liquid crystal molecules of the LC layer 98, and may pass through without the plurality of the polarized outside light changing. As such, the polarized outside light 120 may pass back through the polarizer filter 54 to exit the display 18 as emitted outside light 124. The brightest of the pixel 60, 62 in the "on" state 90 will thus be the emitted light 116 plus the emitted light 124.

When the pixel 60, 62 is in the "off" state 91, as shown in FIG. 12, the liquid crystal switchable retarder pixel 62 may block the outside light 118 from reflecting out of the pixel 60, 62, thereby preserving the contrast of the electronic display 18. In the example of FIG. 12, the self-emissive pixel 60 of the self-emissive pixel array 50 is not emitting any light. Under these conditions, if the outside light 118 were to be reflected off of the pixel 60, 62, the contrast of the "off" self-emissive pixel 60 with other self-emissive pixels 60 that are on may be reduced. As such, by blocking the outside light 118 from being reflected from the pixels 60, 62 while in the "off" state 91, a high contrast may be preserved, even in the present of the outside light 118.

Figure 13:
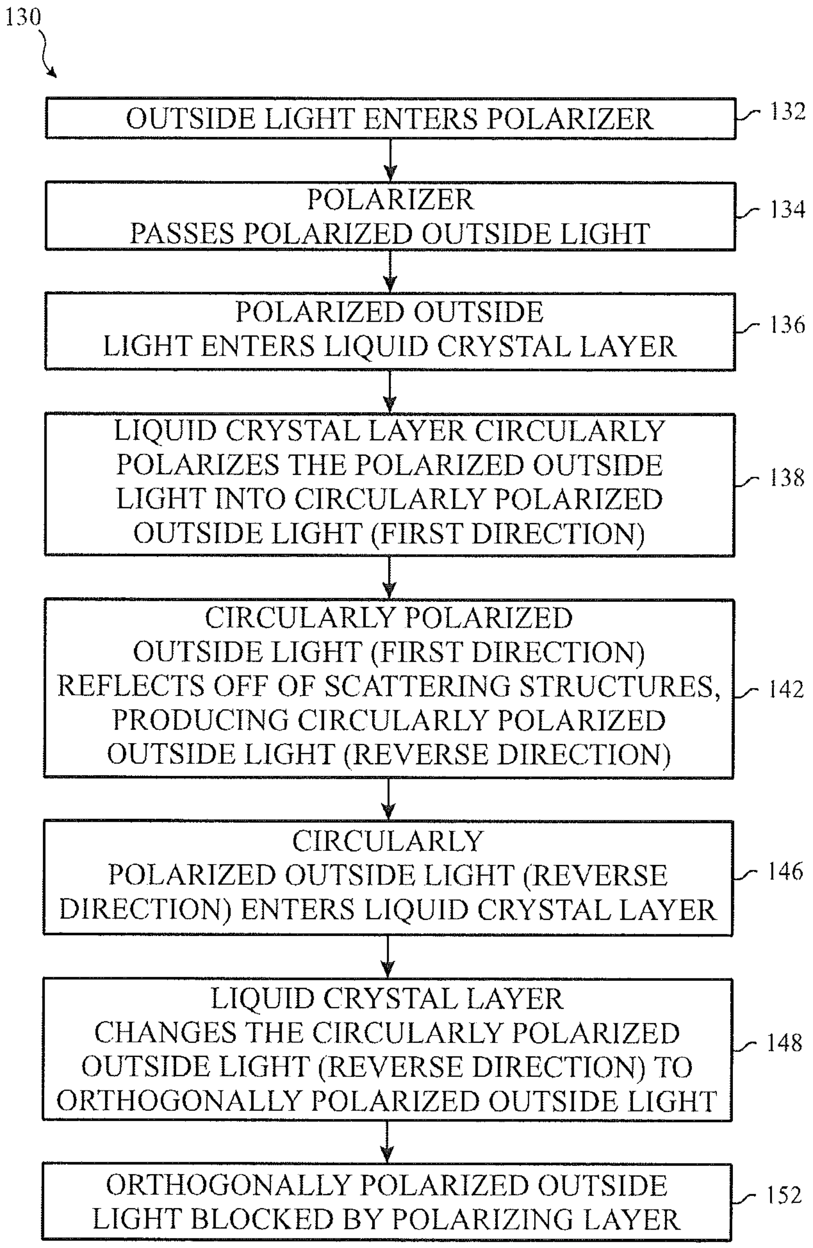
FIG. 13 is a flowchart of a method for using the pixel of the electronic display, as shown in FIG. 12, to selectively block outside light from being emitted at the pixel, in accordance with an embodiment.

The operation of "off" state 91 shown in FIG. 12 is described by a flowchart 130 of FIG. 13. Thus, FIGS. 12 and 13 are described in tandem. In particular, while the pixels 60, 62 are in the "off" state 91, the outside light 118 may enter the polarizer layer 54 (block 132). The polarizer 54 may only allow the polarized outside light 120 to pass and may absorb all other components of the outside light 118 (block 134). In contrast to the "on" state 90 shown in FIG. 11, in the "off" state 91 shown in FIG. 12, the liquid crystal molecules of the LC layer 98 may be tuned not to allow the polarization outside light 120 to pass unchanged. Instead, when the polarized outside light 120 enters the LC layer 98 (block 136), there may be an electric field that tune the LC layer 98 to circularly polarize the polarized outside light 120 (block 138) into circularly polarized outside light (first direction) 140. In effect, when the switchable retarder pixel 62 is in the "off" state 91, the liquid crystal molecules of the LC layer 98 may be tuned to 45° in relation to the transmissive axis of the polarizer layer 54. The thickness of the LC layer 98 may be selected to allow for quarter-wave light retardation.

The circularly polarized outside light (first direction) 140 may reflect off of the scattering structures 122 and becomes polarized in the opposite direction (block 142), becoming circularly polarized outside light (reverse direction) 144. For example, if the circularly polarized outside light of the first direction 140 is right-hand polarized, the circularly polarized outside light (reverse direction) 144 may be polarized in a left-hand orientation. In block 148, the circularly polarized outside light (reverse direction) 144 enters the LC layer 98 (block 146), which causes the circularly polarized outside light (reverse direction) 144 to become orthogonally polarized outside light 150. The resulting orthogonally polarized outside light 150 is orthogonally polarized in relation to the transmissive axis of the polarizer 54. As a result, the orthogonally polarized outside light 150 may be blocked by the polarizer layer 54 (block 152). As a result, when the liquid crystal switchable retarder pixels 62 is in the "off" state 91, the amount of outside light 118 will have a substantially lower impact on the contrast of the display as a whole, since the light 118 will be substantially blocked from becoming part of the light seen reflecting off of the pixel 60.

The electronic display 18 may selectively operate in the high-contrast mode. One method of operating the electronic display 18 is shown by a flowchart 160 of FIG. 14. In the flowchart 160, the electronic display 18 receives image data from the memory 14 or the processor(s) 12 (block 162) and displays the image data using the self-emissive pixels 60 of the self-emissive pixel array 50 (block 164). The electronic display 18 may not always operate in the high-contrast mode. Indeed, when not operating in the high-contrast mode (decision block 166), the liquid crystal switchable retarder pixels 62 may be set all to the same state (block 168). For example, all of the outside light 118 from outside the display 18 may be permitted to be reflected through the pixels 60, 62 (the "on" state) or may be blocked (the "off" state). It should be appreciated that, in at least some embodiments, the electronic display 18 may always operate in the high-contrast mode.

When the electronic display 18 is in the high-contrast mode (decision block 166), the electronic display 18 (e.g., the controller 56 or other display driver circuitry) may set the retarder pixels 62 to the "on" state 90 where the self-emissive pixels exceed a threshold gray level (block 170) and set the retarder pixels to the "off" state 91 where the self-emissive pixels 60 do not exceed the gray level threshold (block 172).

Before continuing, it may be noted that the electronic display 18 may enter the high-contrast mode based on a variety of possible factors. These include, for example, an indication that ambient light has exceeded some ambient light threshold (e.g., as measured by an ambient light sensor of the electronic device 10) or another indication, such as some other indication that electronic display 18 is in a bright environment such as an outdoor environment (e.g., the selection of an "outdoor run" workout by a user of the electronic device 10). Additionally or alternatively, the high-contrast mode may be a mode of operation selectable by a user of the electronic device 10.

Figures 14, 15:
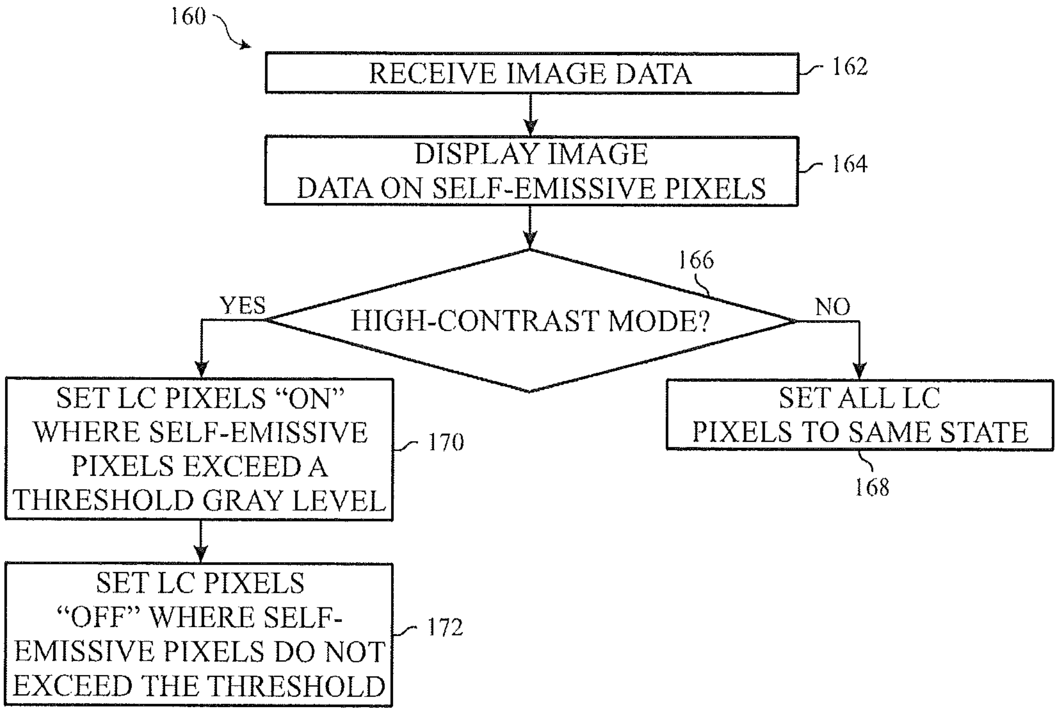
FIG. 14 is a flowchart of a method for operating the using the high-contrast mode, in accordance with an embodiment.
FIG. 15 is a pixel map illustrating setting switchable retarder pixels to an "off" state when corresponding self-emissive pixels are off, in accordance with an embodiment.

A pixel map of FIG. 15 illustrates one manner in which the self-emissive (SE) pixels 60 may be operated in comparison to the liquid crystal (LC) switchable retarder pixels 62 for each of the pixels 60, 62. In the pixel map of FIG. 15, the LC retarder pixels 62 are in the "on" state to allow outside light 118 to enter and exit that pixel when the self-emissive pixel 60 is emitting light of a gray level that is greater than zero. The LC retarder pixels 62 are in the "off" state to block the outside light 118 when the self-emissive pixel 60 is programmed to a gray level of zero (e.g., is not emitting any light).

Alternatively, a pixel map shown in FIG. 16 represents another example in which the liquid crystal (LC) switchable retarder pixels 62 are switched "off" if the corresponding self-emissive (SE) pixel 60 is less than a threshold gray level greater than 0. For instance, in the example of FIG. 16, the liquid crystal retarder pixels 62 are switched "off" any time the self-emissive pixel 60 emits an 8-bit gray level lower than 128. It should be appreciated that the gray level 128 is provided by way of example, and that any suitable threshold gray level may be selected that preserves the contrast of the display 18 while reducing the amount of energy used to switch the liquid crystal retarder pixels 62.

Figure 17:
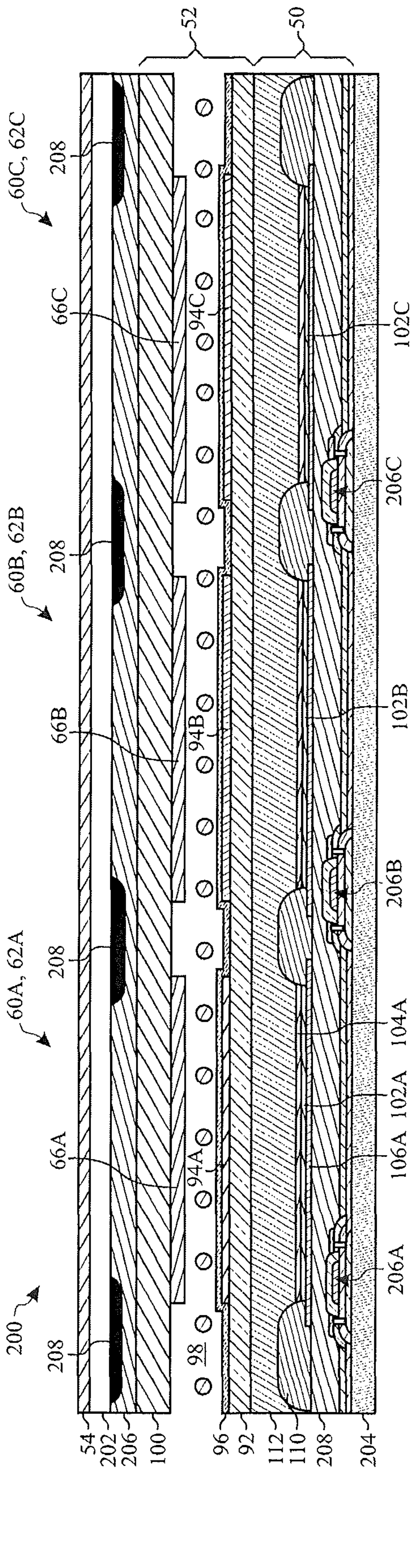
FIG. 17 is a cross-sectional view of three pixels of the electronic display in which the self-emissive pixel is used to reflect outside light through the switchable retarder pixel, in accordance with an embodiment.
Figure 18:
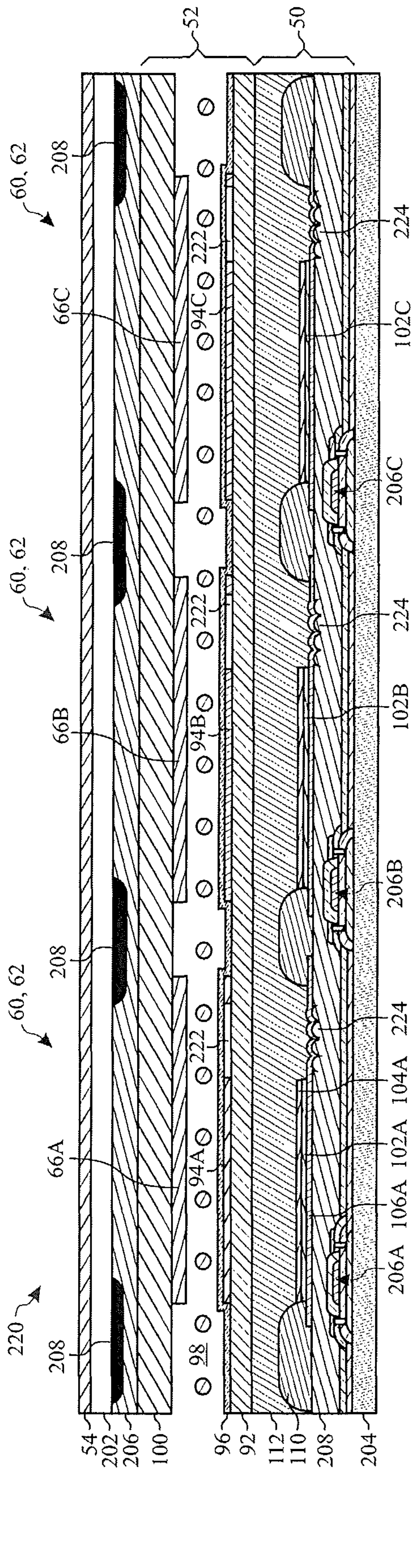
FIG. 18 is a cross-sectional view of three pixels of the electronic display and including a light-window and a light lens to efficiently scatter light entering the pixel from outside and reflect the light back out through the switchable retarder pixel, in accordance with an embodiment.

FIGS. 17 and 18 represent examples of cross-sectional views of a flip thin film transistor (TFT) switchable retarder pixel array 52 coupled to the self-emissive pixel array 50. The cross-sectional views of FIGS. 17 and 18 include three pixels: 60A, 62A (forming a red pixel); 60B, 62B (forming a green pixel); and 60C, 62C (forming a blue pixel). In both FIGS. 17 and 18, the polarizer layer 54 is disposed over a glass layer 202. A corresponding bottom glass layer 204 forms the substrate for the self-emissive pixel array 50. The glass layer 202 forms the substrate (along with the TFT substrate 206 and black matrix 208) for the liquid crystal switchable retarder pixel array 52.

Each pixel 60A, 62A; 60B, 62B; and 60C, 62C contains generally similar structures, with exceptions for the color of the light emitted by that pixel 60, 62. For example, all the pixels 60, 62 include the color filter substrate layer 92, the VCOM layer 96, the LC layer 98, the TFT layer 100, the PDL 110, and the encapsulation layer 112. The specific pixels have different respective pixel electrodes (e.g., 66A, 66B, and 66C) and color filters (e.g., 94A, 94B, and 94C). Likewise, each pixel 60 includes different respective electroluminescent (EL) elements (e.g., 102A, 102B, and 102C), cathodes (e.g., 104A, 104B, and 104C), and anodes (e.g., 106A, 106B, and 106C). FIGS. 17 and 18 also illustrate respective control transistors (e.g., 208A, 208B, and 208C) disposed beneath a power line network (PLN) 210 layer.

The configuration 200 of FIG. 17 does not introduce additional scattering elements. Thus, in the configuration 200, outside light that enters these pixels may reflect off of the various elements of the self-emissive pixel array 50 and exit the pixel when the retarder pixel 62 is in the "on" state. It is believed that the structures of the self-emissive pixel array 50 may provide sufficient reflectivity to enable the light to contribute to the total amount of light in a meaningful way, thereby increasing display contrast. A configuration 220 of FIG. 18 includes certain additional structures that may increase the amount of outside light that can be output by the pixel when the retarder pixel 62 is in the "on" state. These structures may include a window 222 and a light lens 224. Additional outside light may pass through the window 222 with reduced attenuation than otherwise, and may be directed through the color filter 94 by the light lens.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. An electronic display comprising:

a plurality of self-emissive pixels configured to emit first light out of the electronic display based on image data provided to the electronic display;

a plurality of switchable retarder pixels, each of the plurality of switchable retarder pixels corresponding to one of the plurality of self-emissive pixels, the plurality of switchable retarder pixels configured to selectively exclude and permit second light that enters a corresponding self-emissive pixel of the electronic display from outside of the electronic display to be emitted back out of the corresponding self-emissive pixel of the electronic display along with the first light.

2. The electronic display of claim 1, wherein a first portion of the plurality of switchable retarder pixels are in a first state to exclude the second light while a second portion of the plurality of switchable retarder pixels are in a second state to include the second light.

3. The electronic display of claim 1, wherein each of the plurality of self-emissive pixels comprises a micro light emitting diode, an organic light emitting diode, or combination thereof.

4. The electronic display of claim 1, wherein each of the plurality of switchable retarder pixels comprises a liquid crystal pixel.

5. The electronic display of claim 4, wherein the liquid crystal pixel is configured to operate as a quarter-wave plate that causes the second light to have a polarization upon exiting the electronic display that is orthogonal to the polarization upon entering the electronic display.

6. The electronic display of claim 1, wherein each of the plurality of switchable retarder pixels is configured to operate in two states:

an "on" state that permits the second light to be emitted back out of the electronic display; and an "off" state that does not permit the second light to be emitted back out of the electronic display.

7. The electronic display of claim 6, wherein each of the plurality of switchable retarder pixels is configured to operate only in the two states.

8. The electronic display of claim 1, comprising a polarizer layer configured to cause the second light to have a first polarization, wherein each of the plurality of switchable retarder pixels is configured to selectively cause the second light to have the first polarization and to have a second polarization, wherein the second polarization is orthogonal to the first polarization, whereby the polarizer layer emits the second light when the second light has the first polarization but blocks the second light when the second light has the second polarization.

9. A system comprising:

a processor configured to generate image data for an electronic display;

an array of self-emissive pixels configured to display the image data; and an array of switchable retarder pixels, each of the array of switchable retarder pixels corresponding to one of the array of self-emissive pixels, each of the array of switchable retarder pixels configured to:

when in a first state, permit outside light that enters the corresponding self-emissive pixel of the electronic display from outside of the electronic display to contribute to the corresponding self-emissive pixel of the array of self-emissive pixels; and when in a second state, block the outside light from contributing to the corresponding self-emissive pixel of the array of self-emissive pixels.

10. The system of claim 9, comprising control circuitry configured to control whether a state of each of the switchable retarder pixels of the array of switchable retarder pixels is the first state or the second state.

11. The system of claim 10, wherein the control circuitry is configured to enter a first mode that causes all of the switchable retarder pixels of the array of switchable retarder pixels to enter the first state when the array of self-emissive pixels is emitting light and when the array of self-emissive pixels is not emitting light.

12. The system of claim 10, wherein the control circuitry is configured to enter a second mode that causes each of the switchable retarder pixels of the array of switchable retarder pixels to enter:

the first state only when the corresponding self-emissive pixel of the array of self-emissive pixels is emitting light; and the second state when the corresponding self-emissive pixel of the array of self-emissive pixels is not emitting light.

13. The system of claim 10, wherein the control circuitry is configured to enter a second mode that causes each of the switchable retarder pixels of the array of switchable retarder pixels to enter:

the first state only when the corresponding self-emissive pixel of the array of self-emissive pixels is emitting light of a brightness or a gray level, or both, above a threshold level; and the second state only when the corresponding self-emissive pixel of the array of self-emissive pixels is not emitting light of a brightness or a gray level, or both, above a threshold level.

14. The system of claim 9, wherein the array of switchable retarder pixels are configured to be operated in only the first state and the second state.

15. An electronic display comprising:

an array of combined self-emissive pixels and switchable retarder pixels, each of the switchable retarder pixels corresponding to one of the self-emissive pixels of the array of combined self-emissive pixels and switchable retarder pixels, each combined pixel comprising:

a polarizing layer;

a liquid crystal switchable retarder comprising:

a pixel electrode;

a common electrode; and a liquid crystal layer configured to be tuned to two states:

an "on" state that does not substantially alter a polarization of light that passes through the liquid crystal layer; and an "off" state that does substantially alter the polarization of light that passes through the liquid crystal layer; and the self-emissive pixel configured to emit a variable amount of light;

wherein:

when the liquid crystal layer is tuned to the "on" state, light that has entered the combined pixel from outside the electronic display passes through the liquid crystal layer a first time, reflects off of a light-reflective structure inside the combined pixel, passes through the liquid crystal layer a second time, and is permitted to exit by the polarizing layer; and when the liquid crystal layer is tuned to the "off" state, light that has entered the combined pixel from outside the electronic display passes through the liquid crystal layer the first time, reflects off of the light-reflective structure inside the combined pixel, passes through the liquid crystal layer the second time, and is blocked from exiting by the polarizing layer.

16. The electronic display of claim 15, wherein the liquid crystal layer has a thickness configured to enable operation as a quarter-wave plate.

17. The electronic display of claim 15, wherein, when the liquid crystal layer is tuned to the "off" state, the light that has entered the combined pixel from outside the combined pixel:

becomes polarized in a parallel polarization that is parallel to a transmissive axis of the polarizing layer upon passing through the polarizing layer from outside the combined pixel;

becomes circularly polarized in a first orientation upon passing through the liquid crystal layer the first time;

becomes circularly polarized in a second orientation opposite the first orientation upon reflecting off of the light-reflective structure inside the combined pixel;

becomes polarized in an orthogonal polarization that is orthogonal to the transmissive axis of the polarizing layer; and is blocked from exiting by the polarizing layer at least in part because of the orthogonal polarization.

18. The electronic display of claim 15, wherein the liquid crystal layer is configured to be tuned only to the two states.

19. The electronic display of claim 15, wherein the light-reflective structure comprises a component of the self-emissive pixel.

20. The electronic display of claim 15, wherein the light-reflective structure comprises a scattering structure configured to scatter light that reflects off of the light-reflective structure.

21. The electronic display of claim 15, wherein the light-reflective structure comprises a light lens configured to direct at least some light toward other parts of the combined pixel when the light arrives at the light lens substantially perpendicularly to a face of the electronic display.

22. The electronic display of claim 15, wherein each combined pixel comprises a color filter that substantially matches a color of light emitted by the self-emissive pixel of that combined pixel.

23. The electronic display of claim 22, wherein the color filter of at least one of the combined pixels comprises a window configured to permit light to pass without substantially filtering the light by color, thereby allowing more light that has entered from outside the combined pixel to reach the light-reflective structure.

24. A system comprising:

an electronic display that includes an array of self-emissive pixels configured to display an image based on image data and an array of switchable retarder pixels, each of the array of switchable retarder pixels corresponding to a ratio of the array of self-emissive pixels, the array of switchable retarder pixels configured to block at least some outside light that enters from outside of the electronic display from contributing to dark pixels of the image when the electronic display is operating in a high-contrast mode and to allow the at least some outside light that enters from outside of the electronic display to contribute to the dark pixels of the image when the electronic display is not operating in the high-contrast mode; and a processor configured to generate the image data and determine whether to operate the electronic display in the high-contrast mode.

25. The system of claim 24, wherein pixels of the array of switchable retarder pixels corresponds in a 1:1 ratio with pixels of the array of self-emissive pixels.

26. The system of claim 24, wherein pixels of the array of switchable retarder pixels corresponds in a ratio with pixels of the array of self-emissive pixels greater than 1:1.

27. The system of claim 26, wherein pixels of the array of switchable retarder pixels corresponds in a 1:3 ratio with pixels of the array of self-emissive pixels.

28. The system of claim 24, wherein the processor is configured to operate the electronic display in the high-contrast mode based on an indication that the system is in a bright-ambient-light environment.

29. The system of claim 28, comprising an ambient light sensor configured to detect a level of ambient light, wherein the processor is configured to operate the electronic display in the high-contrast mode when the level of ambient light exceeds a threshold.

30. The system of claim 28, wherein the processor is configured to operate the electronic display in the high-contrast mode based at least in part on an indication that the system is being used out of doors.

* * * * *